United States Patent
Stenzler et al.

(10) Patent No.: US 11,090,448 B2
(45) Date of Patent: Aug. 17, 2021

(54) DRY POWDER INHALER AND METHOD OF USE

(71) Applicant: Philip Morris Products S.A., Neuchatel (CH)

(72) Inventors: Alex Stenzler, Long Beach, CA (US); Steve Han, Huntington Beach, CA (US); Arthur Slutsky, Toronto (CA); Steven Ellis, Ontario (CA); Noe Zamel, Toronto (CA); William Alston, San Jose, CA (US)

(73) Assignee: Philip Morris Products S.A., Neuchâtel (CH)

( * ) Notice: Subject to any disclaimer, the term of this patent is extended or adjusted under 35 U.S.C. 154(b) by 473 days.

(21) Appl. No.: 15/566,412

(22) PCT Filed: Apr. 13, 2016

(86) PCT No.: PCT/US2016/027252
§ 371 (c)(1),
(2) Date: Oct. 13, 2017

(87) PCT Pub. No.: WO2016/168274
PCT Pub. Date: Oct. 20, 2016

(65) Prior Publication Data
US 2018/0140790 A1    May 24, 2018

Related U.S. Application Data

(60) Provisional application No. 62/147,808, filed on Apr. 15, 2015.

(51) Int. Cl.
*A61M 15/00* (2006.01)
*A61M 15/06* (2006.01)

(52) U.S. Cl.
CPC ...... *A61M 15/0036* (2014.02); *A61M 15/003* (2014.02); *A61M 15/0021* (2014.02);
(Continued)

(58) Field of Classification Search
CPC ............ A61M 15/003; A61M 15/0036; A61M 15/0038; A61M 15/06; A61M 2202/064;
(Continued)

(56) References Cited

U.S. PATENT DOCUMENTS

| 5,441,060 A | 8/1995 | Rose et al. |
| 6,234,169 B1 | 5/2001 | Bulbrook et al. |

(Continued)

FOREIGN PATENT DOCUMENTS

| CN | 101772361 A | 7/2010 | |
| DE | 19757207 A1 * | 6/1999 | ........ A61M 15/0036 |

(Continued)

OTHER PUBLICATIONS

Definition of "Edge" as described by Merriam-Webster online dictionary. Accessed Jul. 30, 2020. (Year: 2020).*

(Continued)

*Primary Examiner* — Valerie L Woodward
*Assistant Examiner* — Paige Kathleen Bugg
(74) *Attorney, Agent, or Firm* — Mueting Raasch Group (57) ABSTRACT

A device for accessing dry powder within a sealed chamber is described. The device includes a hollow housing having a proximal end opening, a primary distal end opening and a secondary distal end opening, at least one wing structure extending from the outer surface of the housing that is positioned distally from the primary distal opening. Also described is a dry powder inhaler having a housing, a penetrating component for accessing dry powder within a sealed chamber, and a mouthpiece, where the mouthpiece is connected to the proximal end opening of the penetrating (Continued)

component, and wherein the at least a portion of the distal end of the penetrating component is positioned within the inhaler housing.

15 Claims, 10 Drawing Sheets

(52) U.S. Cl.
CPC ........ *A61M 15/0038* (2014.02); *A61M 15/06* (2013.01); *A61M 2202/064* (2013.01)

(58) Field of Classification Search
CPC .......... A61M 25/0612; A61M 25/0618; A61M 25/0637; A61M 15/0033–0041
See application file for complete search history.

(56) References Cited

U.S. PATENT DOCUMENTS

| | | | |
|---|---|---|---|
| 8,508,385 B2 | 8/2013 | Von Schuckmann et al. | |
| 8,561,608 B2 | 10/2013 | Chopard | |
| 2004/0025874 A1 | 2/2004 | Seppala | |
| 2005/0121025 A1* | 6/2005 | Gamard | A61M 15/009 128/200.23 |
| 2007/0295333 A1* | 12/2007 | Fourment | A61M 15/0036 128/203.15 |
| 2008/0251072 A1* | 10/2008 | Lulla | A61M 15/0028 128/203.15 |
| 2009/0090362 A1* | 4/2009 | Harmer | A61M 15/0033 128/203.21 |
| 2010/0192950 A1* | 8/2010 | Chopard | A61M 15/004 128/203.15 |
| 2010/0197565 A1 | 8/2010 | Smutney et al. | |
| 2011/0220106 A1* | 9/2011 | Ganem | A61M 15/0028 128/203.21 |
| 2011/0220234 A1* | 9/2011 | Haas | A61M 15/06 138/109 |
| 2011/0259328 A1 | 10/2011 | Villax et al. | |
| 2015/0045295 A1 | 2/2015 | Smutney et al. | |

FOREIGN PATENT DOCUMENTS

| | | |
|---|---|---|
| JP | 2002165884 A | 6/2002 |
| JP | 2002-522173 T | 7/2002 |
| JP | 2006-522634 T | 10/2006 |
| JP | 2010-531697 T | 9/2010 |
| JP | 2011-504387 T | 2/2011 |
| WO | WO 2004/093848 A2 | 11/2004 |
| WO | WO 2007/007110 A1 | 1/2007 |
| WO | WO 2011/133740 A1 | 10/2011 |
| WO | WO 2014/004400 A2 | 1/2014 |
| WO | WO 2014/089174 A2 | 6/2014 |

OTHER PUBLICATIONS

Translation of DE 19757207 Accessed Nov. 18, 2020. (Year: 1975).*
Supplementary European Search Report, issued by the European Patent Office for corresponding EP Application No. 16 78 0607; dated Nov. 14, 2018; 7 pgs.
International Search Report and Written Opinion from corresponding PCT Application No. PCT/US2016/027252, issued by the United States Patent Office, dated Jul. 18, 2016; 8 pgs.
International Preliminary Report on Patentability from corresponding PCT Application No. PCT/US2016/027252, issued by the International Bureau of WIPO, dated Oct. 26, 2017; 8 pgs.
Japanese Office Action issued for JP 2018-505571 by the Japanese Patent Office, dated Mar. 30, 2020; 7 pgs. including English Abstract.
Chinese Office Action for CN201680032932.1 issued by the Chinese Patent Office dated Oct. 20, 2020; 18 pgs. including English Translation.
Japanese Office Action issued in JP 2018-505571 by the Japanese Patent Office; dated Dec. 3, 2020; 24 pgs. including English Translation.

* cited by examiner

DRY POWDER INHALER AND METHOD OF USE

CROSS-REFERENCE TO RELATED APPLICATIONS

This application is a national stage entry of PCT/US16/27252, filed on Apr. 13, 2016, which claims priority to U.S. provisional application No. 62/147,808 filed on Apr. 15, 2015, both of which are incorporated herein by reference in their entirety.

BACKGROUND OF THE INVENTION

Due to the well documented health hazards of traditional tobacco cigarettes to smokers and bystanders, there has been a shift in the marketplace to find suitable alternatives for the delivery of nicotine to the lungs of a subject. Ideally, nicotine should be delivered to the subject's lungs without the creation of second hand smoke, and without the unpleasant odors associated with traditional tobacco smoking. One mechanism to achieve this is via inhalation of nicotine as a dry powder formulation. In such systems, a dry powder inhaler is used to deposit the powder on the inner surfaces of the lungs for absorption into the bloodstream. Unfortunately though, most dry powder inhalers have numerous undesirable features.

For example, many devices are designed for medical conditions where a patient requires immediate delivery of a medicament. These devices deliver the medicament in a single inhalation. Thus, these devices are not suitable for medicaments that are preferably delivered over several inhalations. Further, these devices rely on air currents that flow directly through or across the medicament which causes some of the medicament to travel at high speed and impact undesired portions of the subject's airway.

Other devices rely on complicated or awkward mechanisms for their use. For example, propellers have been used to rotate a capsule to expel powder by centrifugal force, or various rotating or sliding mechanisms have been used to deposit discrete amounts of powder into the airflow path of an inhaler. These devices are complicated and difficult to use discretely.

Another existing device is shown in U.S. Pat. No. 6,234,169 to Bulbrook ("Bulbrook"), which describes a cone shaped device that protrudes into a dry powder storage reservoir to generate a vortex-like effect inside the cone. The device uses that vortex to dip down inside the storage reservoir and pick up a slug of powder and deliver it to the airways of an individual. However, a significant limitation of the Bulbrook design is that it does not provide adequate energy inside the storage reservoir to deagglomerate the powder sufficiently to deliver the desired aerosol to the user. This is particularly true when the dry powder formulation is contained in a capsule or blister pack, which the device of Bulbrook was not designed for use with.

Thus, there is a need in the art for a dry powder inhaler that creates sufficient turbulence inside a dry powder chamber such that increased amounts of powder can be picked up into the air for inhalation. The present invention satisfies this need.

SUMMARY OF THE INVENTION

Described herein is a device for accessing dry powder within a sealed chamber. The device, also referred to herein as a dry powder inhaler engine, includes a housing having a lumen, at least one proximal end opening to the lumen, a primary distal opening to the lumen and a secondary distal opening to the lumen, and at least one wing structure extending from the outer surface of the housing that is positioned distally from the primary distal opening. In one embodiment, the device includes a penetrating member at the distal tip of the device housing. In another embodiment, the penetrating member has at least one leading edge. In another embodiment, the at least one wing structure is in-line with the at least one leading edge. In another embodiment, the device includes a retaining structure extending from the outer surface of a distal region of the housing. In another embodiment, the retaining structure is positioned proximal to the secondary distal opening. In another embodiment, the primary distal opening is integrated with the retaining structure. In another embodiment, the primary distal opening is positioned proximal to the retaining structure. In another embodiment, the retaining structure is a ring that substantially wraps around the circumference of the device housing. In another embodiment, the at least one wing includes at least one curved region.

A dry powder inhaler is also described. The inhaler includes a housing, a penetrating component for accessing dry powder within a sealed chamber, the penetrating component having a proximal end opening, at least one distal end opening, and at least one wing extending from a distal surface of the penetrating component, and a mouthpiece, wherein the mouthpiece is connected to the proximal end opening of the penetrating component, and wherein the at least a portion of the distal end of the penetrating component is positioned within the inhaler housing. In one embodiment, the penetrating component includes a penetrating member at the distal tip of the component. In another embodiment, the penetrating member includes at least one leading edge. In another embodiment, the at least one wing is in-line with the at least one leading edge. In another embodiment, the inhaler includes a retaining structure extending from the outer surface of a distal region of the penetrating component. In another embodiment, the retaining structure is positioned proximal to the at least one distal opening. In another embodiment, the retaining structure is a ring that substantially wraps around the circumference of the penetrating component. In another embodiment, the at least one wing includes at least one curved region.

A method of delivering dry powder from a sealed chamber to the airway of a subject is also described. The method includes the steps of penetrating the housing a storage chamber containing dry powder with the distal end of a hollow device, wherein the device includes at least one proximal opening, at least one distal opening and at least one wing near the distal end of the hollow device, advancing at least one of the at least one distal openings into the interior of the storage chamber, advancing at least a portion of the at least one wing into the interior of the storage chamber containing dry powder to generate at least one expanded opening in the storage chamber housing, generating a negative pressure within the hollow device by a subject drawing air from the proximal opening in the hollow device via inhalation, and generating a flow of air that enters the storage chamber through the at least one expanded opening, lifts at least a portion of the dry powder within the storage chamber into the flow of air, and passes through the at least one distal opening of the device advanced into the storage chamber, such that the dry powder in the flow of air travels through the hollow region of the device for delivery into a subject's airway via the applied inhalation.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising

FIG. 2, comprising FIGS. 2A and 2B, is a set of schematic views of dry powder storage chambers suitable for use with the dry powder inhaler engine of FIG. 1.

FIG. 2A shows a capsule storage chamber, while

FIG. 3, comprising FIGS. 3A and 3B, is a set of graphs of the elastoplasticity of exemplary storage chamber materials. FIG. 3A shows the typical elastoplastic stress-strain curve of HPMC capsule material, while

FIG. 4, comprising

DETAILED DESCRIPTION

It is to be understood that the figures and descriptions of the present invention have been simplified to illustrate elements that are relevant for a clear understanding of the present invention, while eliminating, for the purpose of clarity, many other elements found in typical dry powder inhalers. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Presented herein are devices, systems and methods for delivering dry powder particles into a subject's airways or/and for absoption into their bloodstream via inhalation. In particular, the functional components or "engine" of a dry powder inhaler ("DPI") are described herein to access the dry powder particles sealed within a storage chamber, lift the dry powder particles into a stream of air, and deliver the airborn particles into the lungs of a user via inhalation.

For example, as shown in FIGS. 1A and 1B, a DPI engine 100 may include at its proximal end a mouthpiece housing 110 having a proximal end opening 120 into a lumen 115 (FIG. 4C) that is continuous or otherwise fluidly connected to the lumen 135 (FIG. 4C) of a cone 130. In the distal region of engine 100 is a retaining ring 140 around at least a portion of the circumference of a distal portion of cone 130. Also in the distal region of engine 100 are one or more wings 160 and a secondary air passage opening 170 into the lumen of cone 130. At the distal tip of engine 100 is a penetrating member 180. The various components of the DPI engine may be composed of plastic or other desirable polymer, or they may alternatively be composed of other rigid materials, such as wood, metals, ceramics and the like. These components may be formed from standard molding, printing or other manufacturing techniques as would be understood by those skilled in the art.

Mouthpiece housing 110 may be integrated with cone 130 to form a continuous unit, or it may be a separate component that is detachable from cone 130. In one embodiment, housing 110, lumen 115 and proximal end opening 120 of the mouthpiece are generally cylindrical. However, it should be appreciated that there is no limitation to the shape or dimensions of any of housing 110, lumen 115 or proximal end opening 120, and accordingly, any shape may be used, as would be understood by those skilled in the art. Preferably, the proximal end of mouthpiece 110 is ergonomically shaped or contoured to most comfortably fit within the mouth of a subject and draw air therethrough via inhalation.

Cone 130 has at least two openings into lumen 135, those being a proximal end opening connecting lumen 135 of cone 130 with lumen 115 of mouthpiece 110, and secondary air passage opening 170 near the distal end of cone 130. Additional openings may exist along the length of housing 110 and cone 130, if desired. In certain embodiments, opening 170 may be a plurality of holes or openings, provided that openings 170 remain inside the dry powder storage chamber when penetrated. Further, opening 170 may be of any size and/or shape desired. For example, opening 170 may be an oblong opening, or an elongated slot, or any other shape desired.

Figure 1A:
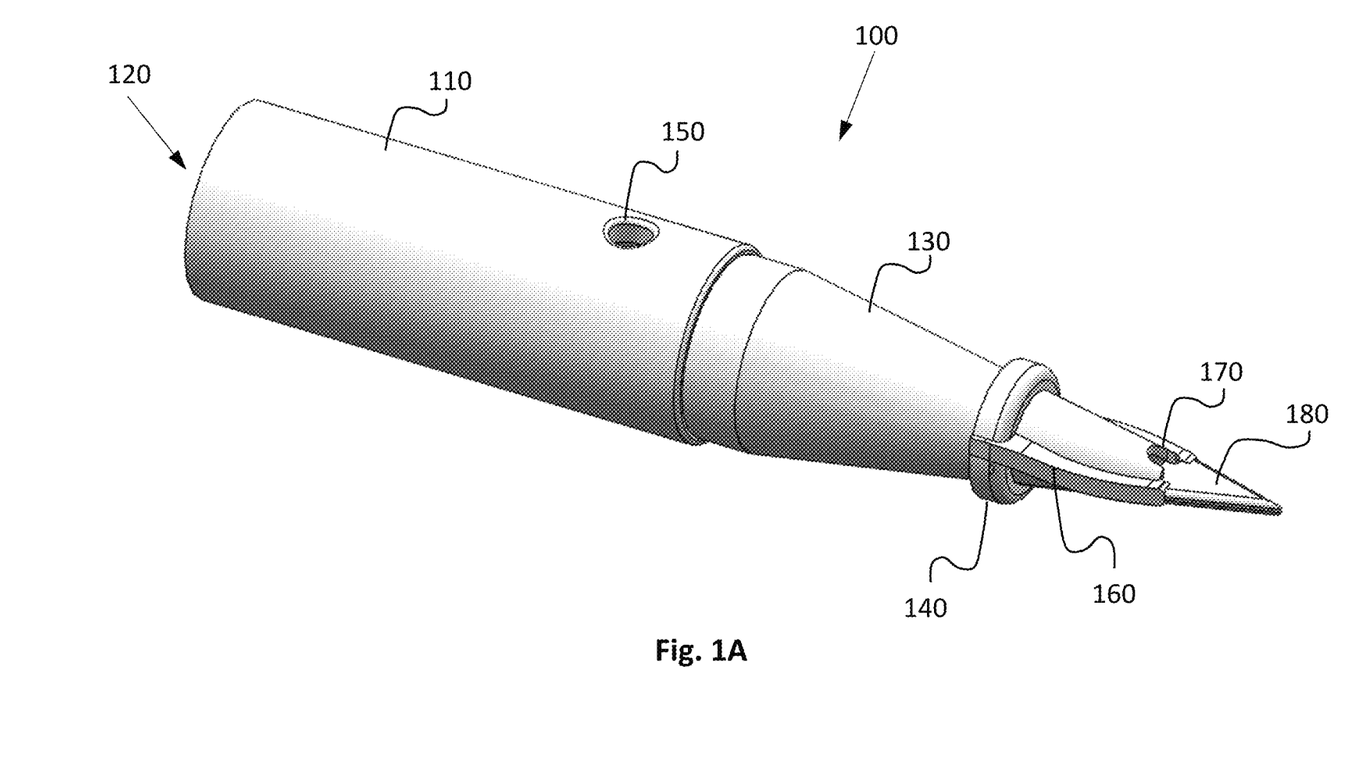
FIGS. 1A and 1B, is a set of schematic views of an exemplary dry powder inhaler engine.
Figure 1B:
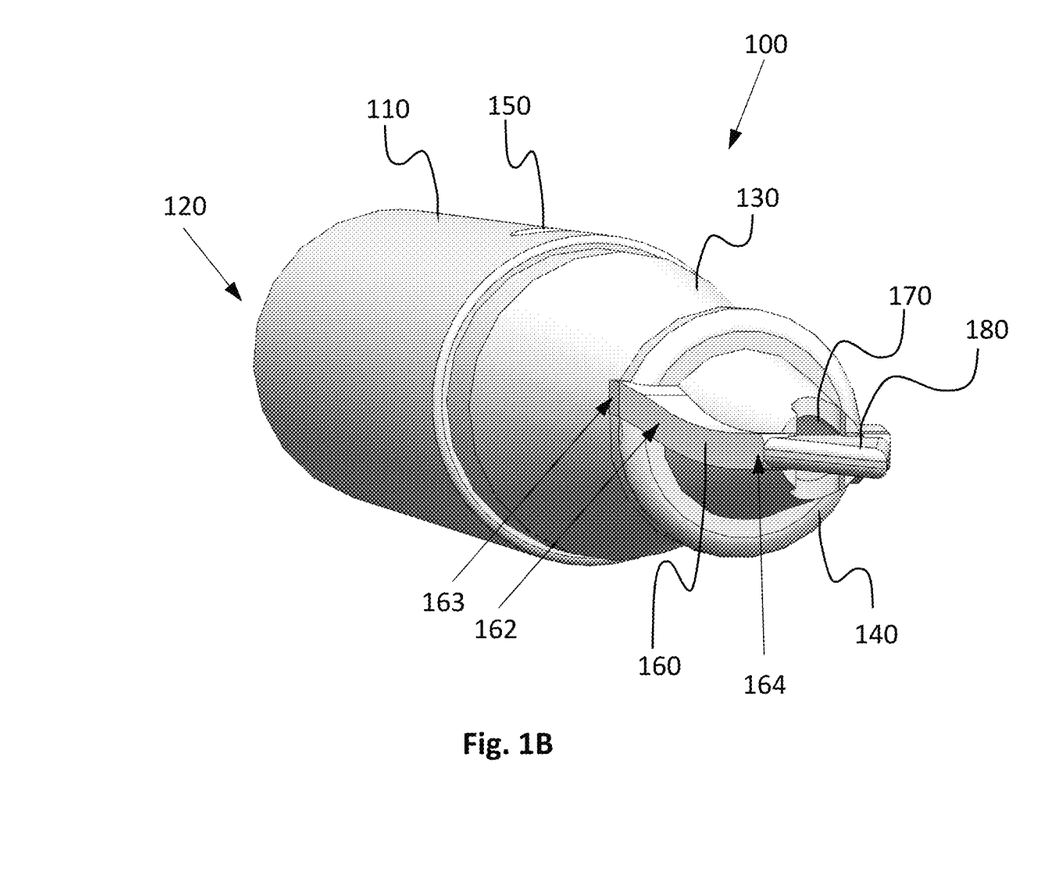

As mentioned previously, cone 130 includes one or more wings 160 along its length distal from retaining ring 140. For example, in one embodiment, cone 130 has a single wing 160. In another embodiment, cone 130 has two wings 160 that are generally opposed to each each other along the surface of cone 130, such as is shown in FIGS. 1A and 1B. Alternatively, cone 130 may have three wings 160 that are radially equidistant from each other along the surface of cone 130. In further embodiments, cone 130 may include two or more sets of opposing wings 160, or may have 5, 7 or 9 radially equidistant wings 160 along the surface of cone 130. In yet another embodiment, one or more wings 160 may be spacially segmented along its length, such that each segmentation space serves as a channel for air to flow therethrough.

Preferably and as shown in FIGS. 1A and 1B, wings 160 may be in-line with and extend proximally from penetrating member 180, such that wings 160 expand the opening in the dry powder storage chamber housing material as the distal tip of DPI engine 100 is advanced therein. In one embodiment, at least one wing 160 is continuous with a leading edge of penetrating member 180, such that the leading edge (or cutting edge) of penetrating member 180 and wing 160 forms a single structure. In another embodiment, wing 160 is in line with, but separate from, the leading edge of penetrating member 180. As shown in FIG. 1B, at least one of the one or more wings 160 includes one or more curvatures or bowed regions 162, such that the connection point 163 of the proximal end of wing 160 connected to retaining ring 140 is ultimately offset from the connection point 164 of the distal end of wing 160 connected to the penetrating member 180. Wings 160 may be generally planar and extend any desired distance outward from cone 130. Further, wings 160 may be of constant or variable thickness along its length. Preferably, the thickness of wings 160 is equal to or greater than the thickness of penetrating member 180. As described herein, the curved wing shape may serve to generate a vortex airflow pattern within the dry powder storage chamber when advanced therein.

Depending on the type of material used to form the housing of the dry powder storage chamber, wings 160 may be sized to either contact the interior surface of the storage chamber when advanced therein, or they may be sized to be free of contact with the interior surface of the storage chamber when advanced therein. Accordingly, there is no limitation to the ultimate number, size and shape of wings 160.

In another embodiment, wings 160 may be constructed with an angled shape distal to the retaining ring 140 that deflects incoming airflow from supplementary airflow entrance hole(s) with intent to form a vortex within the dry powder storage chamber in order to further enhance deagglomeration of powder and further increase the quantity of aerosol delivered to the user.

In another embodiment, wings 160 may include a barb-like structure, wedge or arrowhead structure that is distal to retaining ring 140, such that when the barb, wedge or arrowhead is advanced fully through the storage chamber housing wall, an expanded opening is formed therein to serve as a secondary air inlet into the interior compartment of the storage chamber.

Penetrating member 180 of cone 130 may be generally arrow shaped, to promote an effective puncture and cutting of the housing material of the dry powder storage chamber. Preferably, penetrating member 180 extends distally from secondary opening 170. However, opening 170 may be integrated into all or a portion of penetrating member 180 if desired. Further, it should be appreciated that penetrating member 180 may be any shape suitable for penetrating the storage chamber, as would be understood by those skilled in the art. For example, in one embodiment, penetrating member 180 may include at least one leading edge to effectively pierce and cut the dry powder storage chamber housing as the leading edge contacts and advances into the storage chamber. In another embodiment, penetrating member 180 may be a smooth, piercing tip that is advanced into the storage chamber housing. In still other embodiments, distal secondary opening 170 may be positioned at the distal tip, thereby taking the form of a nozzle. In still other embodiments, no penetrating member is used, and the secondary distal opening 170 is simply advanced into the dry powder storage chamber or other powder reservoir compartment in the inhaler. In such embodiments, the dry powder storage chamber may include a weakened region or a perforation in the chamber housing to facilitate advancement of the distal tip, or the storage chamber may be pre-cut by a separate component of the inhaler. Still further, the distal tip may simply be advanced through a slit valve into a separate dry powder reservoir compartment within the inhaler. Accordingly, as contemplated herein, distal secondary openings 170 may be any size or shape desired, and will generally depend on the optional presence and/or shape of the penetrating member. For example, distal secondary opening may be one or more lateral slots along the distal region of the cone surface, or it may be a single borehole at the distal tip of the cone. It should be appreciated that there is no limitation to the number, size and shape of distal secondary openings 170.

Housing 110 may also include an opening or hole 150 in the housing wall of the mouthpiece, which opens into lumen 115, thereby providing a passageway for air to flow from the external environment into lumen 115. Accordingly, in one embodiment, opening 150 can serve as a chase airflow pathway, such that the velocity of any airborne powder particles drawn into lumen 115 from the dry powder storage chamber can be increased and delivered deep into the lungs, instead of settling in the mouthpiece and/or the user's mouth. Opening 150 may be implemented by closing and opening hole 150 via a valve, the user's finger or any other mechanism for blocking and opening hole 150 to air flow.

Figure 2A:
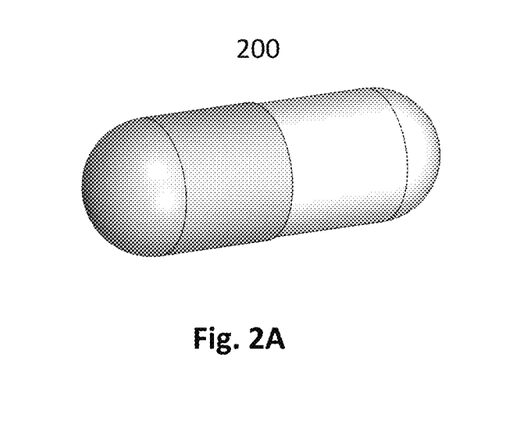
Figure 2B:
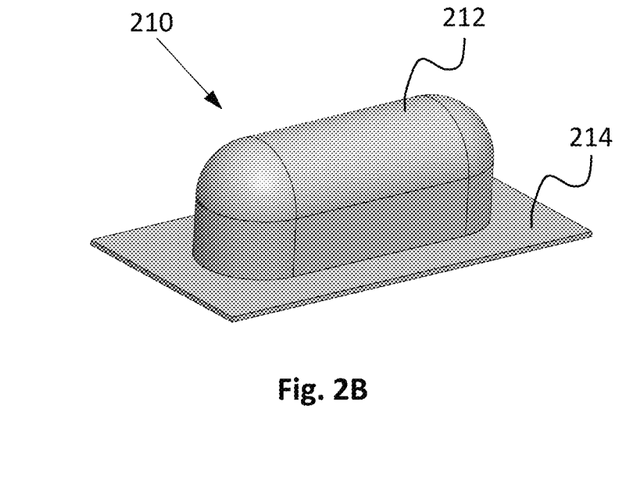
FIG. 2B shows a blister pack storage chamber.

FIGS. 2A and 2B illustrate various types of dry powder storage chambers suitable for use with the DPI engine described herein. For example, as shown in FIG. 2A, the storage chamber may take the form of a capsule 200, such as those typically manufactured from hypromellose (HPMC). In FIG. 2B, the storage chamber may take the form of a blister pack 210, such as those typically manufactured from polyvinylchloride (PVC). Blister pack 210 may generally include a sealed chamber component 212 fixed to a flat surface 214. It should be appreciated that any type of sealed chamber understood by those skilled in the art may be used with the DPI engine, so long as the inhaler housing is suitably designed to allow positioning of the sealed chamber in the inhaler such that the distal tip of the DPI engine may contact and penetrate the sealed chamber within the housing. Preferably, the materials used in the dry powder storage chamber exhibit elastoplastic behavior such that residual plastic deformation is sufficient to form and maintain airflow entry holes when cut or punctured by penetrating member 180 and one or more wings 160 of DPI engine 100.

Figure 3A:
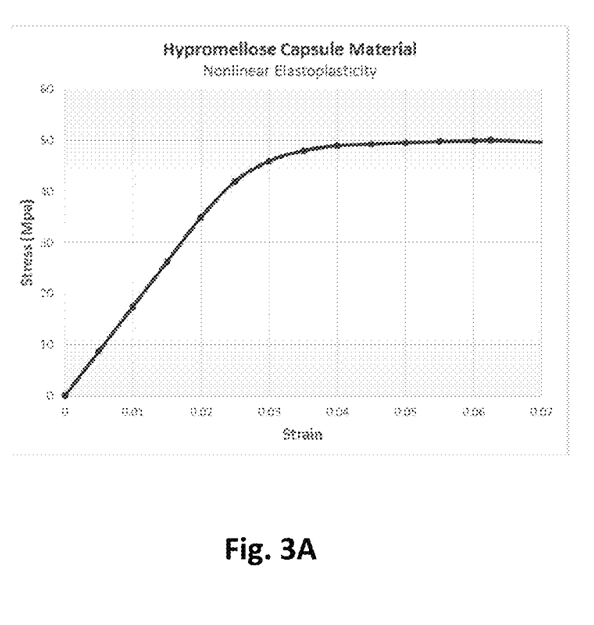
Figure 3B:
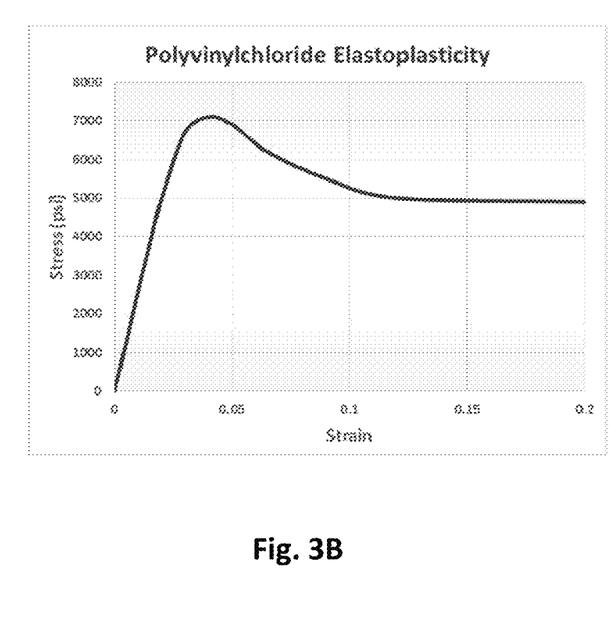
FIG. 3B shows the typical elastoplastic stress-strain curve of PVC blister pack material.

FIG. 3A shows typical elastoplastic stress-strain curve of HPMC capsule material, while FIG. 3B shows typical elastoplastic stress-strain curve of PVC blister material. In these curves it can be seen that typical capsule and blister pack materials exhibit elastoplastic behavior. When deflected below a strain value of 0.03, stress and strain can be approximated by a straight line, or near-perfect elasticity. In this elastic range, material deflected will return to its original shape when the stress is removed. However, if the strain exceeds 0.05, plastic deformation may prevent the material from recovering its original shape. The winged embodiments described herein take advantage of plastic deformation of the container material. Plastic deformation ensures that the secondary holes 220 opened with wings 160 having bowed regions 162 will remain open and not close about the hole by elastic recovery.

Figure 4A:
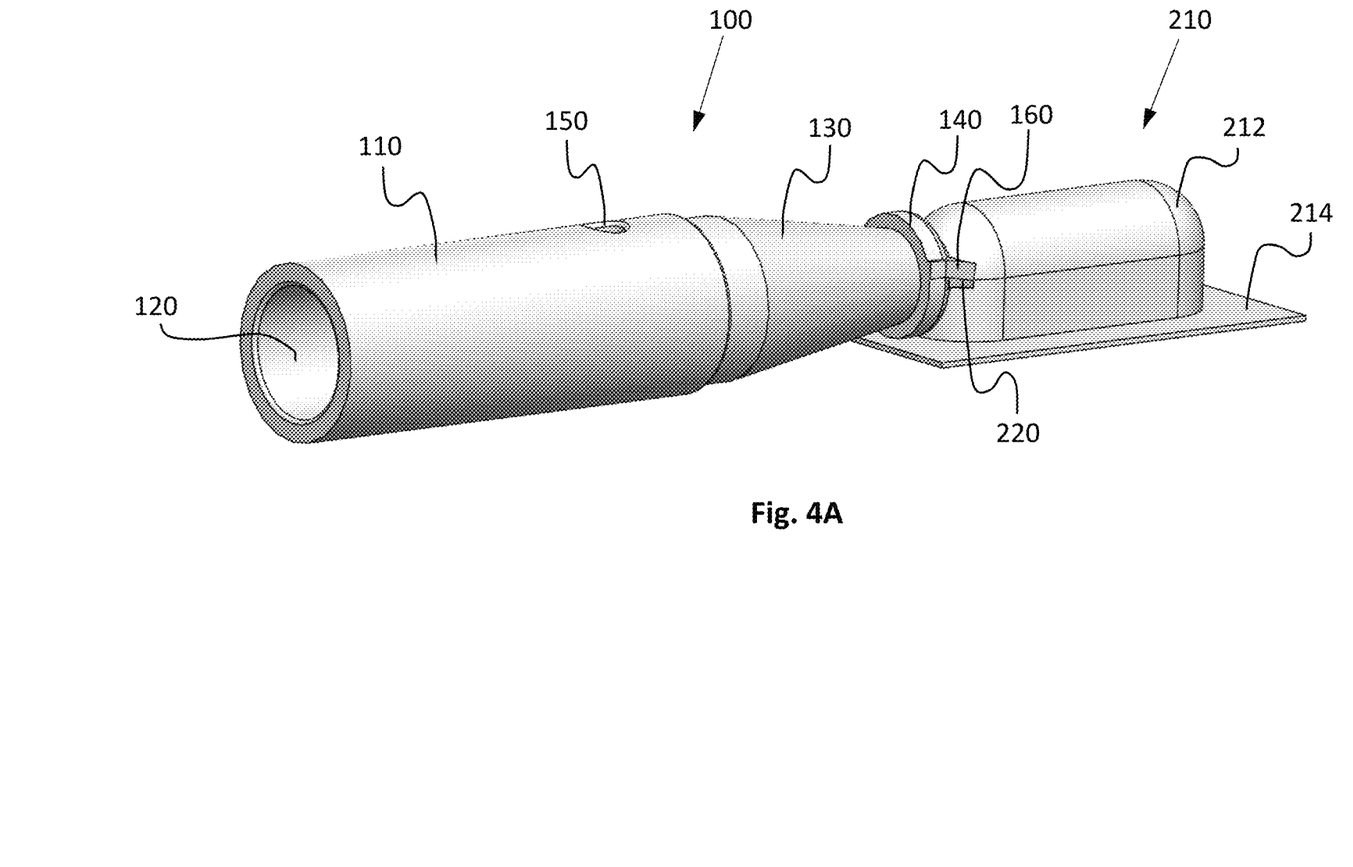
FIGS. 4A-4C, is a set of schematic views of an exemplary dry powder inhaler engine engaging the storage chamber of FIG. 2B.
Figure 4B:
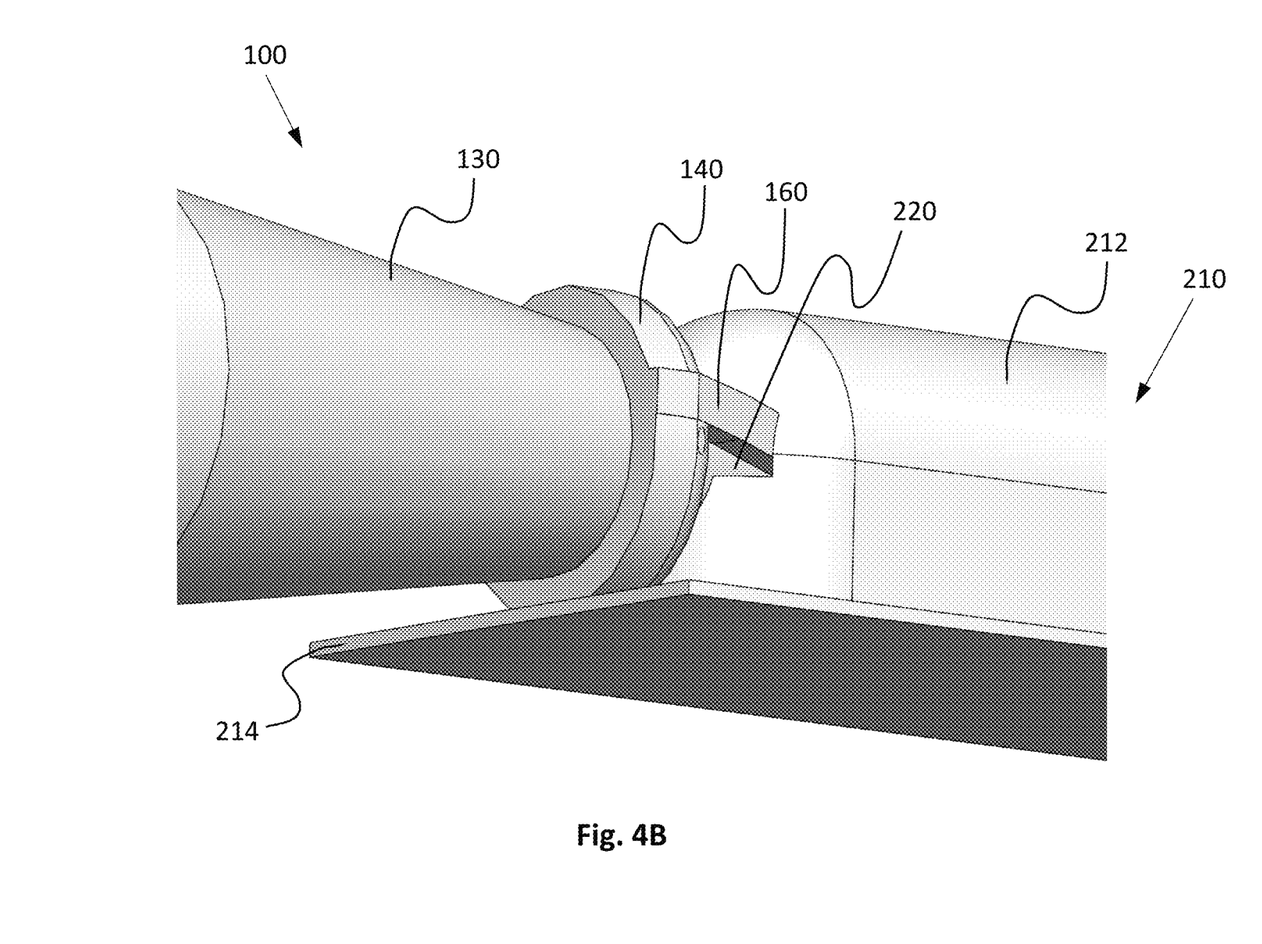
Figure 4C:
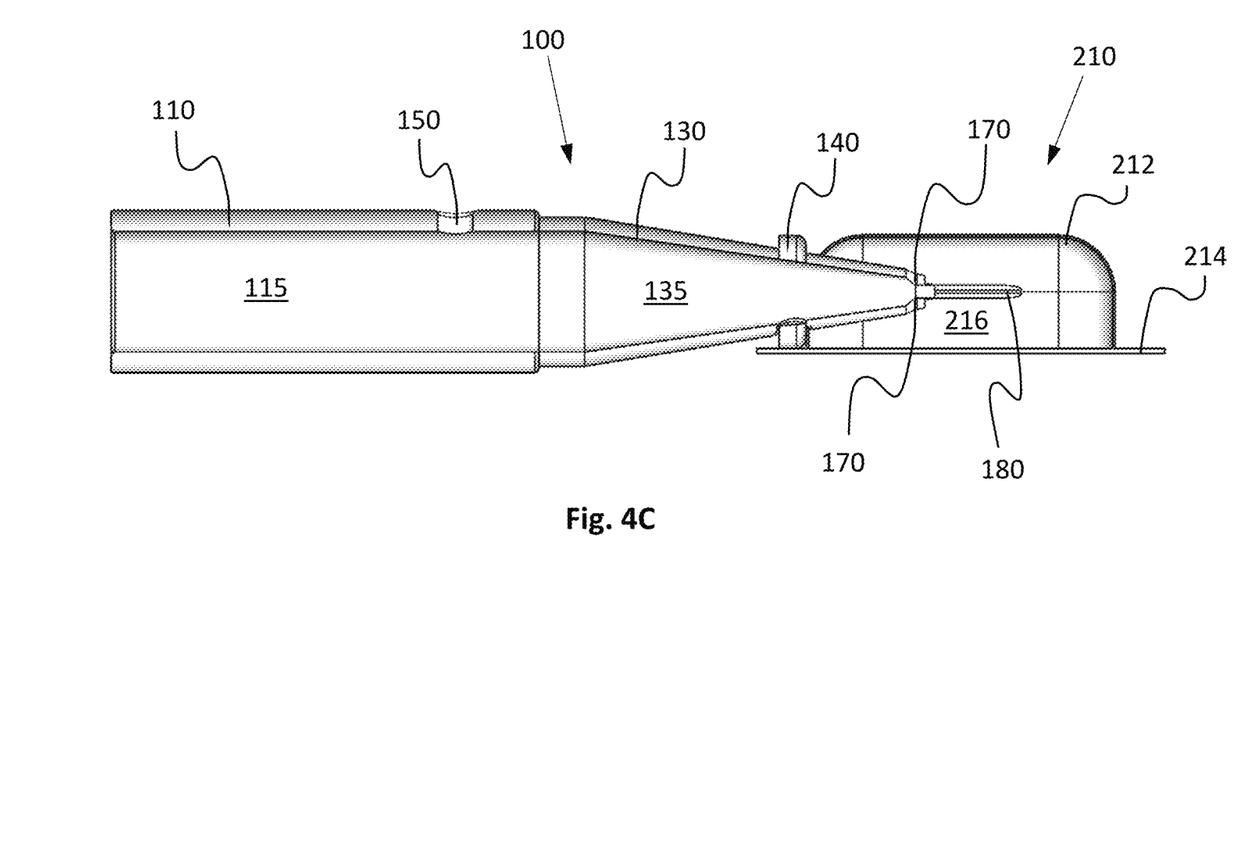
Figure 5:
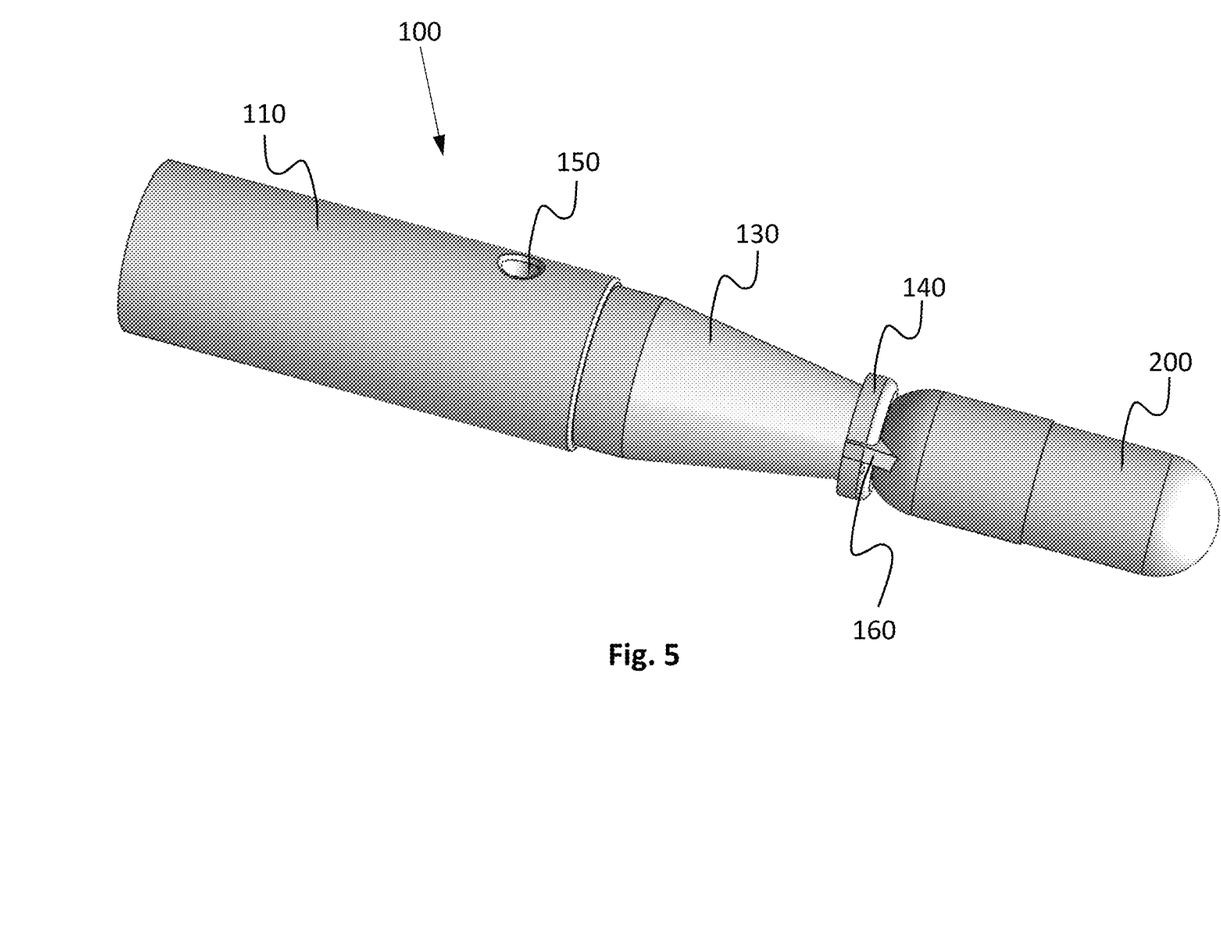
FIG. 5 is a schematic of an exemplary dry powder inhaler engine engaging the storage chamber of FIG. 2A.

Referring now to FIGS. 4A-4C and 5, the DPI engine is illustrated as engaged with a blister pack storage chamber (FIGS. 4A-4C) or a capsule (FIG. 5). While the following illustrations depict the DPI engine generally engaging the storage chamber at an elongated end region of the storage chamber, there is no limitation as to the actual location of penetration and accessing of the internal compartments of the storage chamber by the DPI engine.

As shown in FIGS. 4A-4C, penetrating member 180 is sized and shaped to cut or pierce the housing wall of storage chamber 212. In certain embodiments, flat surface 214 may serve to stabilize and/or secure storage chamber 212 within the inhaler such that it does not undesirably shift or rotate when engaged by the penetrating member 180 of engine 100. After penetrating member 180 cuts or pierces the housing wall of chamber 212, it advances into the interior compartment 216 of chamber 212, thereby creating an opening through which the one or more wings 160 also at least partially advance, until the housing wall of chamber 212 abuts against retaining ring 140. As shown in greater detail in FIG. 4B, when one or more wings 160 pass at least partially through the opening into storage chamber 212, the curved region 162 of wing 160 generates an expanded opening 220 within the housing wall of chamber 212 that is adjacent to wing connection point 163. Accordingly, by advancing wings 160 at least partially through the initial opening created in the storage chamber housing by penetrating member 180, an expanded and uninhibited opening 220 can be formed without applying an axial rotation to cone 130. As shown, expanded and uninhibited opening 220 may serve as a secondary air inlet into interior compartment 216 of chamber 212.

Figure 6:
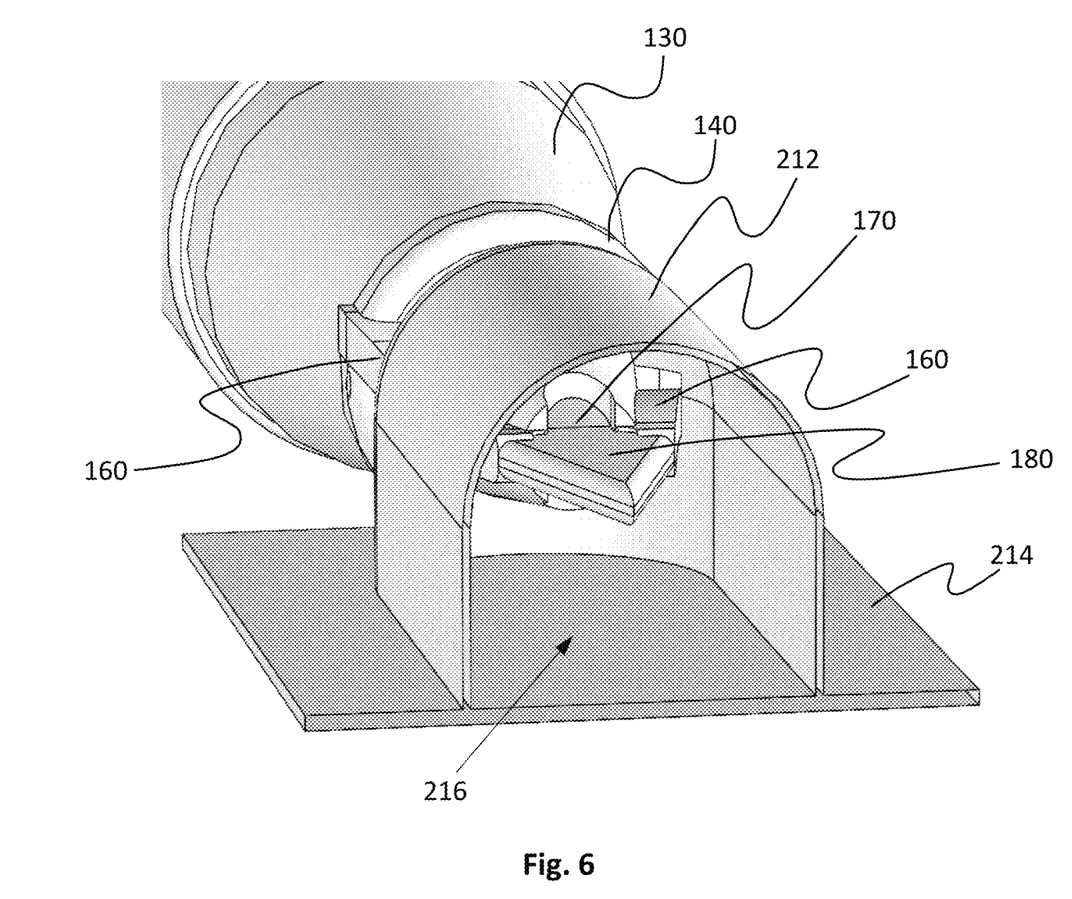
FIG. 6 is a schematic of an exemplary dry powder inhaler engine tip positioned within a storage chamber. The end walls of the storage chamber have been removed to provide a front view of the engine tip within the storage chamber.
Figure 7:
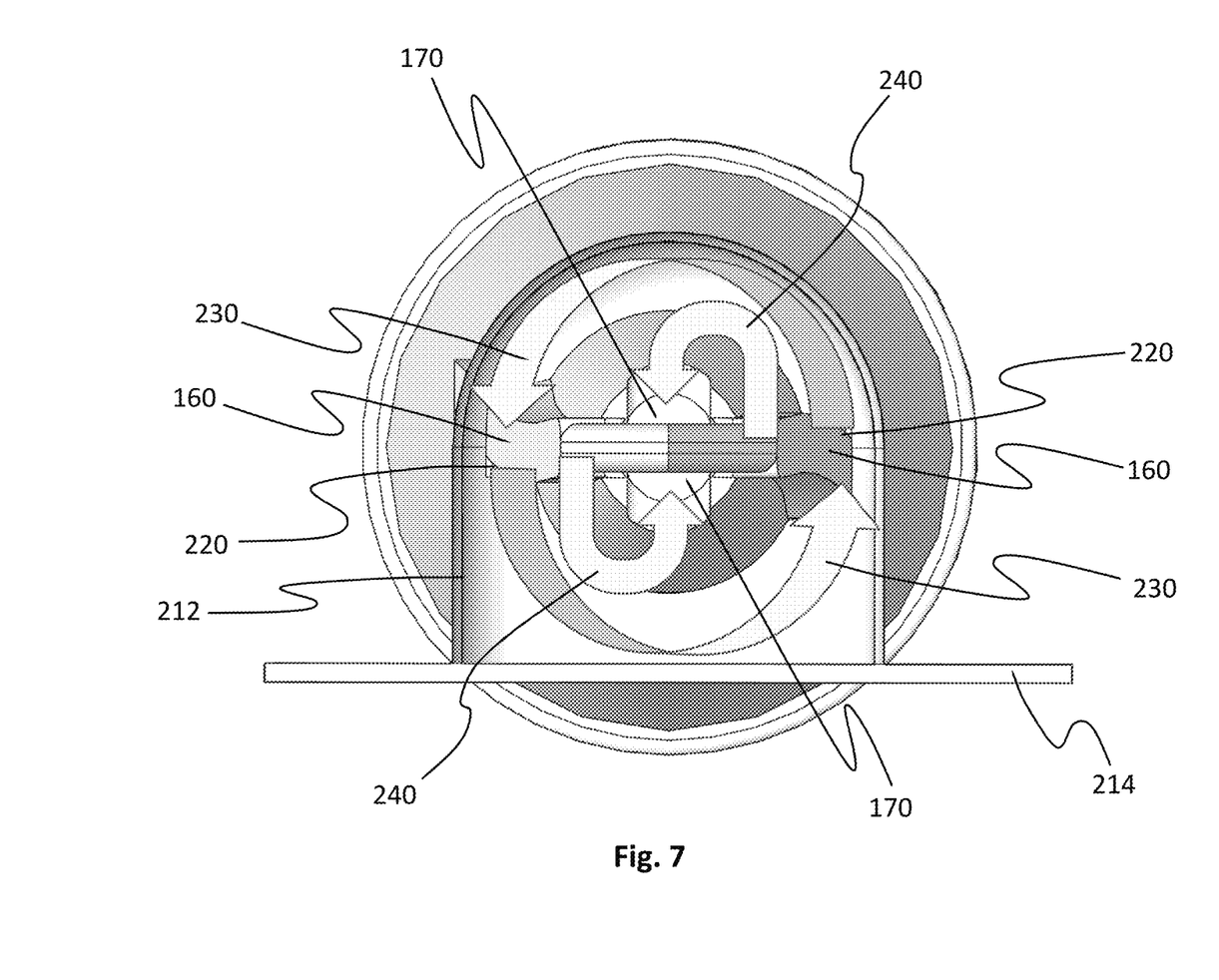
FIG. 7 is a front view schematic similar to FIG. 6, showing an exemplary airflow pattern within the penetrated storage chamber.

In use and with reference to FIGS. 6 and 7, a subject first engages the distal tip of DPI engine 100 with the dry powder storage chamber 210 or 212 and penetrates the chamber housing, such that the DPI engine cone tip is advanced into the interior compartment of the chamber until the retaining ring 140 abuts against the chamber housing wall. Next, the subject may inhale through opening 120 on mouthpiece 110, thereby creating a negative pressure within the lumen 115 of mouthpiece 110 and the lumen 135 of cone 130. This negative pressure draws inlet air from the external environment (e.g., from an internal chamber in which the dry powder storage chamber is positioned) through secondary openings 220 of chamber 212 into the interior compartment 216 where the dry powder resides, and subsequently inlet air from interior compartment 216 enters lumen 135 of cone 130 through distal openings 170. As shown in FIG. 7, wings 160 cause airflow from the second airflow pathway to form a vortex airflow pattern 230 and 240 to dislodge, fluidize and aerosolize powder within interior chamber 216 to flow through distal openings 170 and directed through lumens 135 and 115, and exiting the DPI engine 100 through proximal opening 120 into the subject's lungs. For example, airflow corresponding to arrows 230 depicts airflow entering at secondary openings 220 of chamber 212, where the shape and/or positioning of wings 160 induce rotational flow. Rotational flow then continues down along the interior surface of the chamber housing within interior compartment 216 to dislodge, fluidize and aerosolize the dry powder. With entrained air, the dry powder is then taken into lumen 135 of cone 130 via distal opening 170 via airflow corresponding to arrows 240. Thus, aerosolized powder is subsequently directed through lumens 135 and 115, and exits the DPI engine 100 through proximal opening 120 into the subject's lungs.

Accordingly, a method of delivering dry powder from a sealed chamber to the airway of a subject is provided. The method includes the steps of penetrating the housing a storage chamber containing dry powder with the distal end of a hollow device, wherein the device includes at least one proximal opening, at least one distal opening and at least one wing near the distal end of the hollow device, advancing at least one of the at least one distal openings into the interior of the storage chamber, advancing at least a portion of the at least one wing into the interior of the storage chamber containing dry powder to generate at least one expanded opening in the storage chamber housing, generating a negative pressure within the hollow device by a subject drawing air from the proximal opening in the hollow device via inhalation, and generating a flow of air that enters the storage chamber through the at least one expanded opening, lifts at least a portion of the dry powder within the storage chamber into the flow of air, and passes through the at least one distal opening of the device advanced into the storage chamber, such that the dry powder in the flow of air travels through the hollow region of the device for delivery into a subject's airway via the applied inhalation.

Use of the DPI engine represents a significant and unexpected improvement over existing devices and system, as the DPI engine described and contemplated herein demonstrates significantly increased turbulence within the dry powder storage chamber. Without being limited to any particular theory, this significant and unexpected improvement is in part due to the positioning of the wings near the distal region of the DPI engine. The wings provide two functions. First, they direct the flow of air entering the chamber into a swirling pattern to sweep powder on the interior surfaces of the dry powder storage chamber into the air stream entering the tip of the cone, thereby drawing it into the flow of air to the patient's mouth. Second, the wings spread or expand the opening into the dry powder chamber as the wings move through the chamber housing wall, preferably creating symmetrical and uniform openings for air entrainment. Accordingly, the one or more wings lift significantly more powder and at a greater distance from the DPI engine distal tip openings, and further creates vortices along the interior walls of the dry powder compartment to increase the sweeping of the interior chamber surface to increase powder pickup.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A device for accessing dry powder within a sealed chamber, comprising:
   a housing having a wall defining an outer surface, a proximal end, a distal end and a length therebetween, the housing forming a lumen substantially along the length of the housing, the housing comprising a cylindrical portion forming the proximal end and a conical portion extending from the cylindrical portion and forming the distal end;
   at least one proximal end opening to the lumen, a distal opening extending through the wall to the lumen and an intermediate opening extending through the wall to the lumen between the proximal end opening and the distal opening;
   a penetrating member extending from the distal end of the housing, the penetrating member terminating at a distal tip and comprising a leading edge extending proximally from the distal tip; and
   at least one wing structure extending outward from an outer surface of the conical portion of the housing and positioned distally from the intermediate opening, the at least one wing structure comprising an edge, wherein the edge extends proximally from the penetrating member and wherein the edge is continuous with the leading edge of the penetrating member.

2. The device of claim 1, wherein the at least one wing structure extends along a plane that is in-line with the at least one leading edge.

3. The device of claim 1, further comprising a retaining structure extending from the outer surface of a distal region of the housing.

4. The device of claim 3, wherein the retaining structure is positioned proximal to the distal opening.

5. The device of claim 4, wherein the intermediate opening is integrated with the retaining structure.

6. The device of claim 4, wherein the intermediate opening is positioned proximal to the retaining structure.

7. The device of claim 3, wherein the retaining structure is a ring that substantially wraps around the circumference of the device housing.

8. The device of claim 1, wherein the at least one wing structure includes at least one curved region.

9. A dry powder inhaler comprising the device of claim 1 positioned within at least a portion of the inhaler housing.

10. The device of claim 1, further comprising a hollow mouthpiece connected to the proximal end opening.

11. A dry powder inhaler, comprising:
    a cylindrical housing comprising a mouthpiece with a proximal end opening, the cylindrical housing extending from the proximal end opening to a distal end of the cylindrical housing;
    a penetrating component for accessing dry powder within a sealed chamber, the penetrating component comprising a cone extending from the distal end of the cylindrical housing to a distal end of the penetrating component, the penetrating component comprising:

at least one distal end opening, a penetrating member extending from the distal end of the penetrating component, the penetrating member terminating at a distal tip and comprising a leading edge extending from the distal tip to a proximal end of the penetrating member; and at least one wing extending outward from an outer surface of the cone, the at least one wing comprising an edge, wherein the edge of the at least one wing extends proximally from and is continuous with the leading edge of the penetrating member.

12. The inhaler of claim 11, further comprising a retaining structure extending from the outer surface of a distal region of the penetrating component.

13. The inhaler of claim 12, wherein the retaining structure is positioned proximal to the at least one distal end opening.

14. The inhaler of claim 12, wherein the retaining structure is a ring that substantially wraps around a circumference of the penetrating component.

15. The inhaler of claim 11, wherein the at least one wing includes at least one curved region.

* * * * *